United States Patent [19]

Hegde et al.

[11] Patent Number: 5,837,691
[45] Date of Patent: Nov. 17, 1998

[54] *ACTINOMADURA VULGARIS* SUBSP *VULGARIS* AND ANTIMICROBIAL COMPLEX AND ANTIMICROBIAL

[75] Inventors: Vinod R. Hegde, Parsippany; Ann C. Horan, Summit; Mahesh G. Patel, Verona; Ingrid-Agneta Gunnarsson, Hackettstown, all of N.J.

[73] Assignee: Schering Corporation, Kenilworth, N.J.

[21] Appl. No.: 747,456

[22] Filed: Aug. 12, 1991

Related U.S. Application Data

[63] Continuation of Ser. No. 590,315, Sep. 28, 1990, abandoned, which is a continuation of Ser. No. 227,968, Aug. 3, 1988, abandoned.

[51] Int. Cl.$^6$ .............................. A61K 31/71; C07H 17/08
[52] U.S. Cl. .................. 514/29; 536/7.4; 435/75; 435/825
[58] Field of Search ................ 514/29; 536/17.4, 536/18.7, 7.4; 435/45, 825

[56] References Cited

U.S. PATENT DOCUMENTS 4,474,768  10/1984  Bright ..................................... 536/7.4

FOREIGN PATENT DOCUMENTS 18035  4/1984  Japan .

*Primary Examiner*—Elli Peselev
*Attorney, Agent, or Firm*—Thomas D. Hoffman

[57] ABSTRACT

A novel macrolactam monosaccharide isolated from an antimicrobial complex 517 produced in fermentation under controlled conditions using a biologically pure culture of the microorganism *Actinomadura vulgaris* subsp. *vulgaris* ATCC 53748.

9 Claims, No Drawings

ACTINOMADURA VULGARIS SUBSP VULGARIS AND ANTIMICROBIAL COMPLEX AND ANTIMICROBIAL

This is a continuation of application Ser. No. 07/590,315 filed Sep. 28, 1990, now abandoned which is a continuation of application Ser. No. 227,968 filed Aug. 3, 1988, now abandoned.

This invention relates to a novel macrolactam monosaccharide antimicrobial compound. The compound is isolated from an antimicrobial complex 517 which is produced in fermentation under controlled conditions using a biologically pure culture of the microorganism, *Actinomadura vulgaris* subsp. *vulgaris* SCC 1776, ATCC 53748.

CROSS REFERENCE TO RELATED APPLICATIONS

In related, commonly-assigned co-pending application Ser. No. 07/227,951 (Attorney's Docket No. 2519), filed on the same date as this application, a macrolactam monosaccharide produced by fermentation of *A. vulgaris* subsp. *lanata* subsp. nov. ATCC 53715 is disclosed.

In another related, commonly assigned, co-pending application Ser. No. 07/227,964 (Attorney's Docket No. 2518), filed on the same date as this application, three novel macrolactam monosaccharides produced by fermentation of *A. fulva* subsp. *uruguayensis* sp nov ATCC 53713 are disclosed.

In another related, commonly-assigned co-pending application Ser. No. 07/227,963 (Attorney's Docket No. 2516) filed on the same date as this application, a macrolactam disaccharide produced by fermentation of *A. fulva* subsp. *indica*, ATCC 53714 is disclosed.

SUMMARY OF THE INVENTION

The present invention embraces *Actinomadura vulgaris* subsp. *vulgaris* sp. nov., subsp. nov. SCC 1776, ATCC 53748 and mutants and variants thereof having the identifying characteristics of *Actinomadura vulgaris* subsp. *vulgaris*.

Another aspect of the present invention is directed to the antimicrobial complex 517 produced by cultivating a strain of *Actinomadura vulgaris* subsp. *vulgaris* SCC 1776 having the identifying characteristics of ATCC 53748 in a pH and temperature controlled medium having assimilable sources of carbon and nitrogen under controlled submerged aerobic conditions until a composition of matter having substantial antimicrobial activity is produced.

The present invention is also directed to a component of the antimicrobial complex 517, i.e. a compound represented by the formula 1:

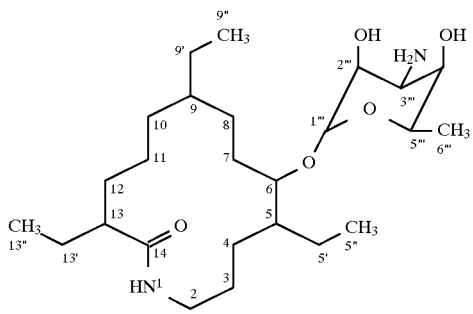

in substantially chemically pure form, or a pharmaceutically acceptable salt thereof.

The Microorganism

The microorganism used for the production of antimicrobial complex 517 and the compound represented by formula 1 is a biologically pure culture of *Actinomadura vulgaris* subsp. *vulgaris* sp. nov., subsp. nov. SCC 1776, ATCC 53748.

A viable culture of this microorganism has been deposited in the collection of the American Type Culture Collection (ATCC) in Rockville, Md., where it has been assigned accession number ATCC 53748. Should the deposited culture become lost, destroyed or non-viable during the longer of the thirty (30) year period from the date the culture was deposited or the five (5) year period after the last request for the deposited culture or the effective life of the patent which issues from this application, the culture will be replaced, upon notice, by applicants or assignee(s) of this application. Subcultures of *Actinomadura vulgaris* subsp. *vulgaris* SCC 1776, ATCC 53748 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

The microorganism was isolated from a sample of soil collected in Borneo. It had been characterized and found to have the microscopic, macroscopic, and whole cell hydrolysis properties of the genus Actinomadura.

Description of the Producing Strain: *Actinomadura vulgaris* subsp. *vulgaris* SCC 1776, ATCC 53748

Source material for the following taxonomic evaluations was a frozen preparation of a pure culture of *Actinomadura vulgaris* subsp. *vulgaris* SCC 1776, ATCC 53748. Inoculum for the biochemical and physiological tests was prepared according to the procedures of Horan and Brodsky [Horan and Brodsky, *Int. J. Syst. Bacteriol.*, Vol. 32, pp. 195–200 (1982)]. The incubation temperature for the biochemical and physiological tests was 30° C. Readings of the results were made at various times up to 21 days for the plate media. Most of the tubed media were read at various times up to 28 days. The tests for decomposition of urea, allantoin and hippurate, as well as the tests for the reduction of nitrates were read for six weeks.

Morphology

Morphological observations of the producing strain of the microorganism of this invention were made on plates of water agar, AV-agar [Nonomura and Ohara, *J. Ferment. Technol.*, Vol. 47, pp. 463–469 (1966)] or modified inorganic salts-starch agar [Difco inorganic salts-starch agar (ISP-4), 12 g; Difco Bacto agar, 15 g; distilled water, 800 ml; soil extract 200 ml; thiamine HCL, 0.5 mg; riboflavin, 0.5 mg; niacin, 0.5 mg; pyridoxine HCL, 0.5 mg; inositol, 0.5 mg; calcium pantothenate, 0.5 mg; p-aminobenzoic acid, 0.5 mg; biotin, 0.25 mg]. Plates were incubated at 30° C. and observed for 4 to 6 weeks.

*A. vulgaris* subsp. *vulgaris* is a gram positive filamentous organism that forms a mycelium differentiated into: (1) a substrate mycelium that penetrates the agar and forms a compact surface layer, and (2) an aerial mycelium that originates from the substrate mycelium. The substrate mycelia are well developed and composed of moderately branching, non-fragmenting hyphae approximately 0.4 μm to 0.8 μm in diameter. Spores do not appear to be present.

The aerial mycelia are approximately 0.5 μm to 1.0 μm in diameter and bear chains having 6 to 29 spores per chain. The spore chains are straight, hooked, irregularly curved or arranged in spirals of 2 to 5 turns. The spirals are most often loosely coiled or may be tightly appressed. The spores are usually round to ovoid, 0.8 μm to 1.1 μm in diameter. The spore surface is irregularly folded. Motile elements are not formed in either the substrate or aerial mycelia.

Chemotaxonomy

Purified cell wall preparations of the producing strain of this invention were analyzed by the method of Becker [Becker et. al., *Appl, Microbiol.*, Vol. 12, pp. 421–423 (1964)] and shown to contain the meso-isomer of 2,6-diaminopimelic acid, alanine, glutamic acid, glucosamine, muramic acid and a trace of mannose. Whole-cell hydroysates were analyzed by the method of Lechevalier [Lechevalier, M. P., *J. Lab. Clin. Med.*, Vol. 71, pp. 934–944 (1968)] and shown to contain glucose, mannose, madurose, ribose, and a trace of rhamnose. The phospholipids present are diphosphatidylglycerol, phosphatidylinositol, phosphatidylinositolmannosides, phosphatidylethanolamine, a trace of phosphatidylmethylethanolamine and unknown glucosamine-containing phospholipids. Thus, the producing strain of the microorganism of this invention has a type III cell wall with a type B whole-cell sugar pattern and a type P IV phospholipid composition [Lechevalier et. al., *Biochem. System. Ecol.*, Vol. 5, pp. 249–260 (1977)], typical of actinomadurae.

Physiological and Biochemical Characteristics

The procedures used to obtain the captional characteristics were those cited by Gordon [Gordon, R. E., *J. Gen. Microbiol.*, Vol. 45, pp. 355–364 (1966)], Luedemann and Brodsky [Luedemann and Brodsky, "*Antimicrob. Agents Chemother.*" pp 47–52 (1965)] and Horan and Brodsky [Horan and Brodsky, *Int. J. Syst. Bacteriol.*, Vol. 32, pp. 195–200 (1982)]. The producing strain, *A. vulgaris* subsp. *vulgaris*, SCC 1776, produces acid from adonitol, D-arabinose, L-arabinose, D-fructose, L-fucose, D-galactose, glucose, glycerol, maltose, D-mannitol, D-mannose, α-D-melibiose, α-methyl-D-glucoside, β-methyl-D-glucopyranoside, D-raffinose, α-L-rhamnose, D-ribose, D-sorbitol, sucrose, D-trehalose and D-xylose but not from dulcitol, i-erythritol, or D-melizitose. Adenine, hypoxanthine, L-tyrosine, elastin, xylan, and hippurate are hydrolyzed but guanine, xanthine and chitin are not. Gelatin is both hydrolyzed and liquified. Starch hydrolysis is negative. Urease and allantoinase are not formed. Nitrate is reduced to nitrite. Melanin and hydrogen sulfide are not formed. Growth does not occur at 10° C. or at 40° C. Growth is fair at 37° C. The microorganism of this invention, *A. vulgaris* subsp. *vulgaris*, SCC 1776, is sensitive to 2% NaCl solution wherein growth is poor. Acetate, formate, lactate, pyruvate and succinate are utilized; benzoate, butyrate and tartrate are not.

*A. vulgaris* subsp. *vulgaris* grows in the presence of 50 μg/ml of gentamicin, rifamycin, erythromycin, penicillin G, cephalothin, novobiocin and spectinomycin, and in the presence of 10 mcg/ml gentamicin, sisomicin, streptomycin and neomycin. Growth is poor in the presence of 50 mcg/ml of sisomicin, neomycin, kanamycin, clindamycin and everninomicin.

Description of *A. vulgaris* subsp. *vulgaris* on Various Media

All plates were incubated at 30° C. and observed at intervals up to 28 days. The common names for the colors were choosen after comparison with color chips from the ISCC-NBS centroid color charts, the "*Color Harmony Manual*", Ed. 4 (Container Corp. America, 1958), or the "*Methuen Handbook of Color*" (Eyre Methuen, London, 1981). On all media tested, the substrate mycelium of *A. vulgaris* subsp. *vulgaris* is pale yellow to yellow-brown. The aerial mycelium is white to ivory. The B-vitamins are not essential for growth but seem to exhance production of aerial mycelia and spores. Yellow-brown soluble pigments are produced. Characteristics are presented in Table I.

Based on the yellow-brown pigmentation of the substrate mycelia, spore morphology and physilogical characteristics *A. vulgaris* subsp. *vulgaris* SCC 1776 (ATCC 53748) appears to be most closely related to *A. vulgaris* subsp. *lanata* ATCC 53715 and *A. spiralis* IFO 14097.

*A. vulgaris* subsp. *vulgaris* ATCC 53748 and *A. spiralis* IFO 14097 differ significantly. In direct comparisons, *A. spiralis* was found to form shorter spore chains (10 to 16 spores per chain); to hydrolyze starch; to form urease and allantoinase; to grow in the presence of 50 mcg/ml of everninomicin but not to grow in the presence of gentamicin, sisomicin and neomycin at 10 mcg/ml; not to hydrolyze xylan or to produce acid from D-sorbitol or sucrose and not to exhibit antibiotic activity.

*A. vulgaris* subsp. *lanata* SCC 1777 is similar to *A. vulgaris* subsp. *vulgaris* ATCC 53748 in substrate mycelial pigmentation, morphology of the spore-bearing hyphae, biochemical and physiological characteristics and antibiotic production. They differ in growth temperature range, resistance to novobiocin and acid production from α-methyl-D-glucoside and D-raffinose. In addition, the macroscopic appearance of the aerial mycelia of *A. vulgaris* subsp. *lanata* SCC 1777 (ATCC 53715) is consistently wooly in texture when compared to *A. vulgaris* subsp. *vulgaris* ATCC 53748. Based on these differences, ATCC 53748 is considered to be a distinct new species designated *A. vulgaris* sp. nov. Shearer, Brodsky and Horan.

In accordance with the Rules of Nomenclature of Bacteria [Lapage, Sneath, Lessel, Skerman, Seeliger and Clark, Ed. 1975 Int. Code of Nomenclature of Bacteria, 1976 rev. Am. Soc. Microbiol., Washington, D.C.] this is both the type strain and the type subspecies, *A. vulgaris* subsp. *vulgaris*.

The species and subspecies names selected (*vulgaris*, L. adj. common, ordinary) refers to the frequency with which this microorganism can be isolated from soil.

TABLE 1

Macroscopic Appearance of *Actinomadura vulgaris* subsp. *vulgaris* SCC 1776, ATCC 53748 on various descriptive media[a]

| MEDIUM | RESULT |
| --- | --- |
| Yeast Extract-<br>Malt Extract Agar (ISP 2) | G: good to excellent<br>AM: present; sparse to moderate; white to ivory (CHM 2db)<br>SC: numerous<br>DFP: present; light yellow-brown<br>SMP: yellow-brown (CHM-2fb, buff, straw |
| Oatmeal Agar<br>(ISP 3) | G: good<br>AM: present; sparse, white<br>SC: numerous<br>DFP: absent<br>SMP: yellow-brown |
| Inorganic Salts-<br>Starch Agar<br>(ISP 4) | G: fair to good<br>AM: present; sparse to moderate, white<br>SC: numerous<br>DFP: absent<br>SMP: yellow-brown |

TABLE 1-continued

Macroscopic Appearance of *Actinomadura vulgaris* subsp. *vulgaris*
SCC 1776, ATCC 53748 on various descriptive media[a]

| MEDIUM | RESULT |
| --- | --- |
| Glycerol-Asparagine Agar (ISP 5) | G: fair to good<br>AM: present; sparse to moderate, white<br>SC: sterile to moderate<br>DFP: absent<br>SMP: yellow (CHM-2ic, lt. gold) to yellow-brown |
| Peptone-Yeast Extract-Iron Agar (ISP 6) | G: fair<br>AM: absent<br>SC: absent<br>DFP: absent<br>SMP: yellow-brown |
| AV Agar | G: fair<br>AM: present abundant, ivory (CHM-2db)<br>SC: numerous<br>DFP: absent<br>SMP: yellow-brown |
| Gauze's Mineral Agar I | G: good<br>AM: present; sparse, white<br>SC: sterile<br>DFP: absent<br>SMP: yellow to yellow-brown |
| ATCC Medium 172 | G: excellent<br>AM: absent<br>SC: absent<br>DFP: present; yellow-brown<br>SMP: yellow-brown |
| Czapek-Sucrose Agar | G: fair to good<br>AM: present; sparse, white<br>SC: sparse<br>DFP: absent<br>SMP: off-white to pale yellow-brown |
| Glucose-Yeast Extract Agar | G: excellent<br>AM: absent<br>SC: absent<br>DFP: absent<br>SMP: yellow-brown |

[a]G = growth; AM = aerial mycelium; SC = spore chain; DFP = diffusible pigment; SMP = substrate mycelium pigmentation

Fermentation of the Microorganism

The antimicrobial complex 517 of this invention is produced when the elaborating microorganism, *Actinomadura vulgaris* subsp. *vulgaris* SCC 1776, ATCC 53748 is grown in an aqueous nutrient medium under submerged aerobic conditions at a temperature of about 27° C. to 40° C., preferably at from 27° C. to 35° C., and at a pH of from about 6.5 to 8.0 with agitation until substantial antimicrobial activity is imparted to the medium. Temperature studies indicate that the organism grows rapidly at about 30° C. Therefore, the fermentation is preferably conducted employing a single temperature pattern of about 30° C. for a period of about 24 to about 96 hours preferably about 90 hours. The fermentation is generally conducted from about 3 to 7 days, preferably for about 3 days.

To determine when peak antimicrobial production has been reached, samples of the fermentation broth were assayed every 24 hours (starting at 48 hrs.) for antimicrobial content by bioassay of the whole broth against *Staphylococcus aureus* ATCC 209P (pH 8.0), *Escherichia coli* ATCC 10536 (pH 8.0) and *Candida albicans* Wisconsin. The growth of the organism (packed cell volume), pH and dissolved oxygen levels are determined either intermittently or continuously.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained potatoe dextrin, cottonseed flour and crushed pea, molasses and maltose as the major sources of nitrogen and carbon, respectively. Under these conditions, the microorganism, SCC 1776, produced antimicrobial complex 517 containing at least seven biologically active components as determined by bioautography against both *S. aureus, E. coli* and *C. albicans* of the complex after development of a thin layer chromatography plate in 8:2 (v/v) chloroform:methanol.

The foregoing media are exemplary of the nutrients utilized by *Actinomadura vulgaris* subsp. *vulgaris* to produce antimicrobial complex 517. However, it is obvious to those trained in fermentation science that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 7.2.

The fermentation was initiated by addition of the inoculum to the broth. Generally, inoculum volume is 5.0% of total broth volume. The inoculum is prepared by addition of a sample of the frozen whole broth to an appropriate medium. A particularly preferred medium comprises beef extract, 0.3%; tryptone, 0.5%; cerelose, 0.1%; potato starch, 2.4%; yeast extract, 0.5%; and calcium carbonate, 0.2% (all percents by weight). The inoculum stage of the fermentation usually requires from 24 to 120 hours with 2 to 4 days preferred and is generally conducted at about 30° C. with agitation. Agitation and a positive air flow, generally about 4.5 L/min. and a temperature of about 30° C. are employed during the fermentation. A particularly preferred fermentation medium comprises potatoe dextrin 2.0%; cottonseed flour 0.75% crushed pea 0.25%; molasses 0.5%; maltose 0.5%; and calcium carbonate 0.4%. The pH of the solution is adjusted to 7.2 prior to the addition of calcium carbonate. An antifoam agent such as SAG (Union Carbide Corp., 50% solution) is added, if necessary, to the fermentors to control foam.

Isolation and Purification of the Antimicrobial Complex 517

The antimicrobial complex 517 of this invention contains a complex mixture of antimicrobials, including as the major component, the compound represented by formula 1, a macrolactam monosaccharide along with a known macrolactam monosaccharide represented by formula 2 and five minor components. The antimicrobial complex 517 of this invention is isolated by extraction of the whole fermentation broth with n-butanol. The n-butanol extract is washed, dried, concentrated, and dissolved in methanol; the so-formed mixture is added to ether:hexane (6:4 v/v). The so-formed precipitate is the antimicrobial complex 517 of this invention which exhibits antifungal activity against *Candida spp.* and antibacterial activity against gram positive and negative bacteria.

Isolation and Purification of the Compound of this Invention (Formula 1)

The compound of formula 1 was obtained as the major antimicrobial component of the antimicrobial complex 517 by preparative High Performance Liquid Chromatography (HPLC) of antimicrobial complex 517 on a silica gel column using as the eluate a mixture of chloroform:methanol:triethylamine (95:5:0.5, v/v/v).

The compound represented by formula 1 is a white solid, basic in nature and gives a positive color reaction with ninhydrin. The compound is fairly soluble in methanol, dimethyl sulfoxide, sparingly soluble in ethyl acetate and insoluble in water and also shows a white lipid like spot on TLC plate when sprayed with water.

The physicochemical data for the compound represented by formula 1 are shown in Table II.

TABLE II

PHYSIOCHEMICAL DATA FOR COMPOUND OF FORMULA 1

| | |
|---|---|
| Opt. Rot | $[\alpha]_D^{26} = -5.8$ (CH$_3$OH, c 0.5) |
| UV λmax | End Absorption |
| IR(KBr) | 3420, 3300, 2920, 1640, 1555, 1385, 1050 cm$^{-1}$ |
| FAB MS | 457(M + H), 312, 294, 163, 146 |
| PMR(CD$_3$OD + CDCl$_3$) δ | 0.85(t, 3 —CH$_3$), 1.25(d, —CH$_3$), 1.0–1.7(CH$_2$ & CH), 2.05(m, 1H), 3.03(dd, CH), 3.3(m, CH), 3.4–3.7 (several CH), 4.9(d, 1H). |
| Molecular Formula | C$_{25}$H$_{48}$N$_2$O$_5$ |

The compound represented by formula 2 hereinbelow was isolated from antimicrobial complex 517 as a white crystalline solid:

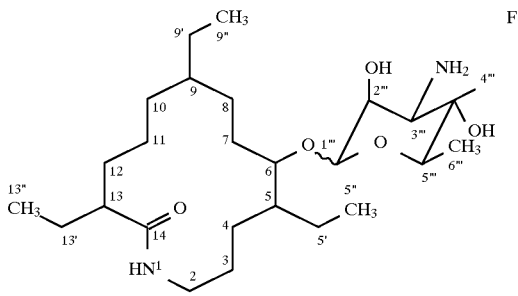

Formula 2

We determined that (1) the compound of formula 2 is basic in nature and shows a positive color reaction wth ninhydrin, is fairly soluble in methanol and dimethyl sulfoxide, sparingly soluble in ethyl acetate and chloroform and insoluble in water, and (2) the compound of formula 2 like all the components from antimicrobial complex 517 is lipophillic in nature and shows a white lipid like spot on TLC plates which are sprayed with water. Physiochemical data for compound of formula 2 are given in Table III.

TABLE III

PHYSIOCHEMICAL DATA FOR COMPOUND OF FORMULA 2

| | |
|---|---|
| Opt. Rot | $[\alpha]_D^{26} = +9.7$(c 0.5, MeOH) |
| UV λmax | End Absorption |
| IR (KBr) | 3420, 3300, 2930, 1640, 1550, 1455, 1045 cm$^{-1}$. |
| FAB MS | 457.3674(M + H) |
| Mol. Formula | C$_{25}$H$_{48}$N$_2$O$_5$ |
| PMR(CD$_3$OD + CDCl$_3$) | 0.82(t, CH$_3$), 0.89(t, 2-CH$_3$) 1.25(d, CH$_3$), 1.0–1.8(CH$_2$ & CH) 2.05(m, 1H), 2.90(dd, 1H), 3.00(bd, 1H), 3.25(t, 1H) 3.65(m, 1H), 3.75(bd, 1H), 4.80(d, 1H). |

The Carbon-13 NMR data for the compounds of formulas 1 and 2 are given in Table IV

TABLE IV

COMPARISON OF CMR DATA OF COMPOUNDS OF FORMULA 1 AND 2

| Carbon | Compound of Formula 1 | Compound of Formula 2 |
|---|---|---|
| CH$_3$ | 8.95, 12.26, 12.60 16.68 | 8.95, 12.28, 12.56 17.67 |
| CH$_2$ | 21.57, 21.82, 22.79 25.51, 25.57, 26.94 27.69, 28.08, 32.57, 33.93, 39.20 | 21.47, 21.74, 22.69, 25.55, 25.55, 26.90, 27.63, 28.07, 32.55, 33.90, 39.21 |
| CH | 38.95, 41.24, 49.40, 50.86, 62.89, 67.47, 69.33, 77.59, 97.50 | 38.95, 41.22, 50.66, 53.84, 69.82, 71.00 72.91, 76.95, 97.49 |
| CO | 178.23 | 178.17 |

The compound of formula 1 is levorotatory with a specific rotation of $[\alpha]_D^{26}=-5.8$ and has no UV absorption. FAB mass spectrum shows (M+H)$^+$ peak at 457 and thus, the molecular weight of the compound of formula 1 is 456. The characteristic peaks in IR at 1640 and 1550 cm$^{-1}$ indicate the presence of an amide. The physicochemical data of Tables II, III and IV and derivatization and degradation studies on the compounds of formula 1 and 2 are consistent with a macrolactam monosaccharide having the structure represented by the formula I.

The Biological Activity of the Antimicrobial Complex 517, and the Compound of Formula 1

The antimicrobial complex 517 of this invention exhibits both antifungal activity and antibacterial activity in vitro against Gram positive and Gram negative microorganisms.

The compound represented by formula 1, isolated from the antimicrobial complex 517, exhibits in vitro antifungal in a Sabouraud dextrose broth medium against seven species of Candida (geometric mean MIC of 2.0 mcg/mL) and six species of dermatophytes (geometric mean MIC of 101.6 mcg/mL) and antifungal activity against seven species of Candida (geometric mean MIC of 6.56 mcg/mL) in Eagles Minimum Essential Medium.

Pharmaceutical Compositions

This invention also contemplates antimicrobially effective pharmaceutical compositions comprising an antimicrobially effective amount of a compound of formula 1 or pharmaceutically acceptable salts thereof in admixture with a pharmaceutically acceptable, non-toxic carrier adapted for topical, oral or parenteral use.

The preferred pharmaceutically acceptable salts are non-toxic acid addition salts formed by adding to the compound of formula 1 about a stoichiometric amount of a mineral acid, such as HCl, HBr, H$_2$SO$_4$ or H$_3$PO$_4$, or of an organic acid, such as acetic, propionic, valeric, oleic, palmitic, stearic, lauric, benzoic, lactic, para-toluene sulfonic, methane sulfonic, citric, maleic, fumaric, succinic and the like.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 0.1 to 10 grams of a compound of formula 1 per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

In general, the dosage of compound of formula 1 administered to combat a given microbial infection is similar to the dosage requirements of the present commercial products miconazole, clotrimazole, and ketoconazole.

In general, the topical dosage range of the compound of formula 1 administered to combat a given microbial infection is from about 0.2% to about 10% by weight of a particular pharmaceutical composition formulated in single or divided doses, with the preferred range being about 0.5% to about 4% and with the most preferred range being about 1% to about 2%.

In general, the oral dosage for humans of the compound of formula 1 administered to combat a given microbial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula 1 administered to combat a given microbial infection ranges for about 0.1 mg per kilogram of body weight per day, to about 20 mg per kilogram of body weight per day, in single or divided doses, with about 1 mg per kilogram of body weight per day being preferred.

It will be appreciated that the actual preferred dosages of the compound of this invention or pharmaceutically acceptable salts thereof will vary according to the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the invention:

EXAMPLE 1

Preparation of the Antimicrobial Complex 517 of This Invention

The compound of formula 1 was produced as the major component of antimicrobial complex 517 by natural strain selection of the *A. vulgaris* subsp. *vulgaris*, SCC 1776, ATCC 53748.

A. Inoculum Preparation

1) Initial Stage

Prepare a 250 mL Erlenmeyer flask with 50 mL of the following germination medium:

| Beef Extract | 3 g |
| --- | --- |
| Tryptone | 5 g |
| Yeast Extract | 5 g |
| Cerelose | 1 g |
| Potato Starch | 24 g |
| Calcium Carbonate | 2 g |
| Tap Water | 1000 mL |
| AF-1* | 1 mL |

*AF-1 is an antifoam agent available from Dow Corning Corp., Midland, MI 48641.

Sterilize the broth and after cooling, add 2.5 mL of a frozen whole broth sample of the microorganism of this invention from a previously prepared inoculum to each flask broth. Incubate at 30° C. with continual agitation at 300 rpm for 48 hours.

2) Second Stage

Transfer 25 mL of the first stage germination broth to each of twenty 2-liter Erlenmeyer flasks, each containing 350 mL of the same germination medium and which had been previously pH adjusted and sterilized. Incubate at 30° C. with continual agitation at 300 rpm for 48 hours.

B. Fermentation

In a 150 fermentor, add 100 L of the following medium:

| | g/l |
| --- | --- |
| Potatoe Dextrin | 20.0 |
| Cottonseed Flour | 7.5 |
| Crushed Pea | 2.5 |
| Molasses | 5.0 |
| Maltose | 5.0 |
| CaCO$_3$ | 2.0 |
| Tap Water | 1000.0 mL |
| Antifoam (SAG 471 Union Carbide 50% Solution) | 1.0 mL |

Adjust the pH of the medium to 7.2 and then sterilize the medium. Inoculate the fermentation medium with 700 mL of the second stage inoculum preparation of Step A. Incubate the fermentation mixture at 30° C. with 18 cubic feet per minute of air flow and 400 rpm agitation for about 72 hours.

C. Isolation

Extract 100 L of the whole fermentation broth produced in accordance with the fermentation procedure hereinabove with two 50 L volumes of n-butanol. Concentrate the combined n-butanol extracts to 2 L and wash the 2 L concentrate three times with 2 L of water. Concentrate the washed n-butanol extracts to dryness and dissolve the concentrate in 200 mL of chloroform: methanol (1:1, v/v). Add to the so-formed solution, 5 L of diethyether:hexane (5:2, v/v) to produce 9.5 g of crude antimicrobial complex 517 comtaining the compound of formula 1 as the major component.

Purify the crude antimicrobial complex 517 on preparative HPLC (Water Associates, Preparative 500) using silica gel cartridges and as eluent chloroform:methanol:triethylamine (95:5:0.5, v/v/v) to produce 1.18 g of the compound of formula 1 as a white solid m.p.: 216°–220° C. (dec). The white solid is substantially chemically pure, basic in nature, gives a positive color reaction with ninhydrin, is fairly soluble in methanol, dimethylsulfoxide, is sparingly soluble in ethyl acetate and insoluble in water. The physicochemical data for the compound of formula 1 are summarized in Tables II and IV.

What is claimed is:

1. A macrolactam monosaccharide antimicrobial compound which is represented by the formula 1

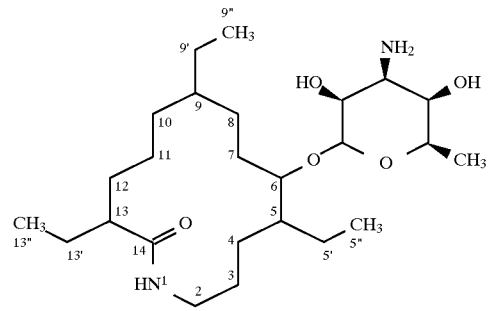

wherein the sugar attached to C-6 of the compound of formula 1 is a 3-amino-3,6-dideoxytalopyranoside, (a) is a white solid, basic in nature and gives a positive color reaction with ninhydrin;

(b) soluble in methanol, dimethyl sulfoxide and insoluble in water;
(c) has an optical rotation: $[a]_D^{26}=-5.8$ ($CH_3OH$, c 0.5);
(d) has only end absorption in the UV;
(e) has an infraed Spectrum: 3420, 3300, 2920, 1640, 1555, 1385, and 1050 $cm^{-1}$ (KBr);
(f) has a FAB Mass Spectrum: 457(M+H), 312, 294, 163, and 146;
(g) has PMR $\partial$ values (ppm): ($DC_3OD+CDCl_3$): 0.85(t, 3-$CH_3$), 1.25(d, —$CH_3$), 1.0–1.7($CH_2$ & CH), 2.05(m, 1H), 3.03(dd, CH), 3.3(m, CH), 3.4–3.7(several CH), 4.9(d, 1H); and
(h) has a Molecular Formula: $C_{25}H_{48}N_2O_5$; in substantially chemically pure form, or a pharmaceutically acceptable salt thereof.

2. A pharmaceutical composition comprising an antimicrobially effective amount of the compound of claim 1 and a pharmaceutically acceptable carrier or diluent.

3. The pharmaceutical composition of claim 2 suitable for parenteral administration.

4. The pharmaceutical composition of claim 2 suitable for topical administration.

5. The pharmaceutical composition of claim 2 suitable for oral administration.

6. A method for treating a bacterial infection in a host having a susceptible bacterial infection which comprises administering to said host an antibacterially effective amount of the compound of claim 1 or a pharmaceutical composition thereof.

7. The method of claim 6 wherein the route of administration is parenteral.

8. The method of claim 6 wherein the route of administration is topical.

9. The method of claim 6 wherein the route of administration is oral.

* * * * *